US011141062B2

(12) United States Patent
Geissler et al.

(10) Patent No.: US 11,141,062 B2
(45) Date of Patent: Oct. 12, 2021

(54) SYSTEM AND METHOD FOR ANIMAL LOCATION TRACKING AND HEALTH MONITORING USING LONG RANGE RFID AND TEMPERATURE MONITORING

(71) Applicant: Geissler Companies, LLC, Minneapolis, MN (US)

(72) Inventors: Randolph K. Geissler, Hudson, WI (US); Steve A. Lewis, Bloomington, MN (US)

(73) Assignee: GEISSLER COMPANIES, LLC, Minneapolis, MN (US)

( * ) Notice: Subject to any disclaimer, the term of this patent is extended or adjusted under 35 U.S.C. 154(b) by 0 days.

(21) Appl. No.: 16/214,430

(22) Filed: Dec. 10, 2018

(65) Prior Publication Data

US 2020/0178800 A1     Jun. 11, 2020

(51) Int. Cl.
*G08B 23/00* (2006.01)
*A61B 5/00* (2006.01)
(Continued)

(52) U.S. Cl.
CPC .......... *A61B 5/0008* (2013.01); *A01K 11/004* (2013.01); *A61B 5/01* (2013.01);
(Continued)

(58) Field of Classification Search
CPC ....... A61B 5/0008; A61B 5/6839; A61B 5/01; A61B 5/6815; A61B 90/98;
(Continued)

(56) References Cited

U.S. PATENT DOCUMENTS 6,559,620 B2    5/2003    Zhou et al.
6,724,309 B2    4/2004    Grose et al.
(Continued)

OTHER PUBLICATIONS

QAG, https://quantifiedag.com/, https://quantifiedag.com/cattle-ear-tags/, https://quantifiedag.com/our-cattle-management-system/, https://quantifiedag.com/about-animal-health-management/, 27 pages.

*Primary Examiner* — Tanmay K Shah
(74) *Attorney, Agent, or Firm* — Berg Hill Greenleaf Ruscitti LLP (57) ABSTRACT

The invention includes a location tracking device in an RFID environment, a system and method for tracking tag objects. Preferred embodiments include location tracking for livestock and a system and method for categorizing animal health. The location tracking device is an active or passive RFID device having a low power, long range transceiver for tracking the location and movement of the tag animal. The RFID device further includes a temperature reader circuit that induces an activation voltage on an inductive coupled temperature sensor having an LC circuit. The activation voltage is selectively cycled on and off to measure the decay of the LC circuit by its resonant frequency. Changes in capacitance of the LC circuit are converted to temperature readings thereby providing temperature monitoring of the animal. The system and method includes logic in the form of predetermined movement categories which indicate whether an animal may be potentially sick or healthy. The movement categories include frequency of movement and distances traveled by a monitored animal.

9 Claims, 3 Drawing Sheets

(51) Int. Cl.
  *H04W 4/80* (2018.01)
  *G06K 7/10* (2006.01)
  *A61B 5/01* (2006.01)
  *A61B 90/98* (2016.01)
  *A01K 11/00* (2006.01)

(52) U.S. Cl.
  CPC .......... *A61B 5/6815* (2013.01); *A61B 5/6839* (2013.01); *A61B 90/98* (2016.02); *G06K 7/10366* (2013.01); *H04W 4/80* (2018.02); *A61B 2503/40* (2013.01); *A61B 2560/0214* (2013.01)

(58) Field of Classification Search
  CPC ........ A61B 2503/40; A61B 2560/0214; G06K 7/10366; H04W 4/80; A01K 11/004
  USPC ...................................................... 340/573.3
  See application file for complete search history.

(56) References Cited

U.S. PATENT DOCUMENTS

| | | | |
|---|---|---|---|
| 6,749,566 | B2 | 6/2004 | Russ |
| 6,878,052 | B2 | 4/2005 | Andersson |
| 7,026,941 | B1 | 4/2006 | Anderson |
| 7,062,308 | B1 | 6/2006 | Jackson |
| 7,619,522 | B2 | 11/2009 | Geissler |
| 7,843,350 | B2 | 11/2010 | Geissler et al. |
| 7,969,307 | B2 | 6/2011 | Peeters |
| 3,019,662 | A1 | 9/2011 | Lucas |
| 8,159,338 | B2 | 4/2012 | Breed |
| 8,334,768 | B2 | 12/2012 | Eaton et al. |
| 8,896,423 | B2 | 11/2014 | Brumer et al. |
| 9,011,333 | B2 | 4/2015 | Geissler et al. |
| 9,060,679 | B2 | 6/2015 | Stewart |
| 9,195,866 | B1 | 11/2015 | Mehranfar et al. |
| 9,247,292 | B2 | 1/2016 | Belz et al. |
| 9,373,014 | B1 | 6/2016 | Mehranfar |
| 9,504,387 | B2 | 11/2016 | Alonsoperez Lanza |
| 9,642,529 | B1 | 5/2017 | Siddiqui |
| 9,788,057 | B2 | 10/2017 | Belz et al. |
| 9,826,714 | B2 | 11/2017 | Garrity |
| 9,894,884 | B2 | 2/2018 | Hill et al. |
| 10,039,267 | B1 | 8/2018 | Thiex et al. |
| 10,242,547 | B1* | 3/2019 | Struhsaker ............ A01K 29/005 |
| 10,349,632 | B2 | 7/2019 | Shame et al. |
| 2004/0000713 | A1* | 1/2004 | Yamashita .............. H01L 35/32 257/728 |
| 2005/0030160 | A1 | 2/2005 | Goren et al. |
| 2005/0145187 | A1 | 7/2005 | Gray |
| 2006/0066449 | A1 | 3/2006 | Johnson |
| 2010/0259393 | A1* | 10/2010 | Marur .............. G06K 19/07749 340/572.8 |
| 2011/0169610 | A1 | 7/2011 | Geissler et al. |
| 2011/0181399 | A1* | 7/2011 | Pollack .............. G06K 19/0717 340/10.33 |
| 2012/0050046 | A1 | 3/2012 | Satorius |
| 2015/0363563 | A1 | 12/2015 | Hallwachs |
| 2016/0367188 | A1 | 12/2016 | Malik et al. |
| 2017/0006838 | A1 | 1/2017 | Brayer et al. |
| 2017/0156288 | A1 | 6/2017 | Singh |
| 2017/0202185 | A1 | 7/2017 | Trumbull et al. |
| 2017/0270323 | A1* | 9/2017 | Butler ................ G06K 7/10198 |

\* cited by examiner

SYSTEM AND METHOD FOR ANIMAL LOCATION TRACKING AND HEALTH MONITORING USING LONG RANGE RFID AND TEMPERATURE MONITORING

FIELD OF THE INVENTION

The invention generally relates to radio frequency identification (RFID) used in tracking locations of livestock, and more particularly, to an RFID device, system and method for animal location tracking and health monitoring that uses a long range RFID capability combined with a temperature monitoring feature.

BACKGROUND OF THE INVENTION

RFID technology is commonly used in many different commercial and industrial settings for accurately tracking and recording locations of objects. In an industrial setting, RFID technology is used to track the locations of various products as they are manufactured, shipped, and delivered for consumption. In an agricultural setting, RFID technology is known for use with animal tags that are used to identify livestock within confined location such as a feed yard.

RFID devices may be generally categorized as active, passive, or semi active/passive. Active RFID devices incorporate a transponder with its own power source. Passive RFID devices incorporate a transponder that receives power from an interrogator or base station. Hybrid or semi active/passive devices may include a transponder that has its own power source, but may also receive supplemental power from the interrogator or base station.

Radiofrequency identification employs electromagnetic fields to automatically identify objects that incorporate RFID tags. An RFID tag includes electronically stored information in the form of electronic registers that store data that may allow the tag to be uniquely identified among a plurality of other RFID tags. As mentioned, RFID tags are utilized within many different commercial settings. Examples of uses of RFID tags include tags for livestock, RFID tagged pharmaceuticals, RFID tags for component identification of objects within a manufacturing process, and others.

Active RFID tags intermittently transmit an ID signal for authentication. A battery assisted passive tag also has an integral battery power source, but is not activated unless in the presence of an RF signal generated by an RFID reader. A passive tag has no onboard power source and rather, uses the radiofrequency energy transmitted by the reader to power the tag. Further, tags may be read only or read/write. For read-only tags, a pre-assigned serial number and other data may be incorporated in the read-only register(s) of the tags. Read/write tags are those in which object specific data is written into the tag by a user/administrator.

Within the subset of passive RFID tags, there are two general types, namely, capacitively coupled tags or inductively coupled tags. Based on current manufacturing techniques, inductively coupled RFID devices have a greater effective range and are therefore preferred to minimize the number of interrogation fields required at a particular location where animals are tracked and monitored.

As for the basic structure of an RFID tag, it includes an integrated circuit or "chip" for storing and processing information, modulating and demodulating an RF signal, collecting power from the incident reader signal. The tag further includes an antenna for receiving an interrogation signal and transmitting an identification signal. Specific tag information is typically stored as nonvolatile memory and incorporates logic for processing transmission and sensor data. The logic can be programmable by a user or preprogrammed.

A common construction for a capacitively coupled passive RFID tag includes a transponder with an integral microprocessor that is powered by a metal coil that surrounds the transponder. The coil serves dual functions as a power producing inductance element as well as an antenna to receive radio frequency signals from an interrogation field. The coil configuration generates an electrical current that powers the microprocessor. The microprocessor has stored data that is used to uniquely identify the tag, such as by a unique serial number, along with any other programmed data that may correspond to the tag. When the tag is energized by the interrogation field, the transponder generates a return signal including the programmed data uniquely corresponding to the tag.

An RFID reader transmits an encoded radio signal to interrogate the tag. After interrogation, the tag replies with a relatively low power transmission signal that identifies the tag. Tag authentication typically includes a unique serial number and other product related information which may identify, for example, the specific type of product associated with the tag. Since each tag may be assigned a unique serial number, a RFID reader can distinguish between many tags that might be within the range of the RFID reader.

In the livestock industry, passive RFID systems are preferred because a large number of RFID tags may be required and passive RFID tags are more cost effective to manufacture since they do not have their own power source (which is typically a battery). Passive RFID tags have other advantages including being relatively smaller and lighter than active RFID tags.

While passive RFID tags are commonly used in the livestock industry, there are a number of inherent problems associated with the use of such tags. In accordance with regulatory requirements of a particular country in which an RFID tag may be used, standard transmission frequencies have been established. In the US, the standard radio frequency for livestock tags is currently 134.2 kHz. It is impractical to conduct location tracking using 134.2 kHz passive ID tracking because the read range of the RFID tags is very limited to approximately three feet from a reader antennae. Because of FCC power limitations in the U.S., it is not possible to raise the power of the readers to the required amount to overcome the limited read range. It is also not practical to add the significant number of additional reader antennae to compensate for the limited read range. Accordingly, the standard transmission frequency adopted in the US presents substantial obstacles to RFID location tracking One example of a reference that discloses a radiofrequency animal tracking system to address various problems associated with passive RFID systems includes the U.S. Pat. No. 7,619,522. This reference provides a transponder that can communicate over at least two different frequencies so that real-time performance of the transponder can be improved without losing backwards compatibility. The system also provides for the capability for in end user to customize and program identification tags that allows a user to track other data associated with tags employed in the field. In one embodiment, the reference discloses an RFID tag comprising a first antenna, a transponder coupled to the antenna, the transponder including a first transmission unit, first memory in first power circuitry wherein the first power circuitry is configured to receive a current induced in the first antenna to power the first transmission unit and first memory. The first transmission unit is also configured to retrieve data stored in the first memory and to transmit at least a portion of the data through the first antenna on the first carrier frequency and on a second carrier frequency.

Another reference that discloses an improved RFID tracking capability is the U.S. Pat. No. 9,826,714. Specifically, this reference discloses RFID tags that have low power, long range transmission capabilities. Power is drawn from a battery or a renewable energy source such as an integral PV circuit. The tags incorporate a microcontroller having a sleep mode that enables nearly no quiescent current draw when the micro controller is in the sleep mode. The micro controller may remain in the sleep mode for long periods of time following a short period of data transmission to a low-power long-range transmitter. The tags may also include sensors for determining an ambient temperature or biometric data regarding the animal to which the tag is attached. Locations of tracking tags may be determined using signal trilateration and/or signal triangulation.

Despite the number of enhancements for use of RFID technology in connection with location tracking of objects, there are still a number of shortcomings. In the field of livestock management, RFID tags are routinely used at feedlot locations however the vast majority of RFID tags solutions still suffer from drawbacks to include insufficient power for activating passive tags and insufficient range. As set forth below in reference to the present invention, it provides certain advantages over the prior art to include greater range and enhanced capabilities for discrete location tracking of individual tags within the monitored location.

SUMMARY OF THE INVENTION

The invention includes an RFID location tracking device or tag and an associated RFID system and method. The invention provides for animal location tracking and health monitoring that uses a long range RFID capability combined with an integrated temperature monitoring feature thereby creating a multi-functional RFID tagging capability.

In accordance with preferred embodiments of the invention, an RFID tracking device is especially adapted for use in connection with cattle tags, wherein the device includes a low power, long range transceiver or radio transmitter that is capable of transmitting signals over relatively long distances as compared to prior radio transmitters. A preferred low power, long-range transceiver for use is one that implements the LoRa® protocol. One example of a long-range transceiver is a commercially available Semtech® SX1280 radio transceiver. LoRa® radio transceivers have a much greater range than prior 2.4 GHz Bluetooth radios. In the environment of a feed yard, the range of a LoRa® transceiver can extend well over 1 km versus a few hundred feet for prior Bluetooth type radios. Another feature Incorporated within LoRa® radio transceivers includes a time of flight measurement that can be used to calculate the distance between the RFID reader and the transmitting RFID tags in the field. Hereinafter, the terms "low power, long range" or "long range" as used to describe radio transmissions means radio transmissions that are compatible with the LoRa® protocol developed by Semtech®. This protocol is a spread spectrum modulation process derived from chirp spread spectrum (CSS) technology for wireless transmissions. This protocol has become the most widely accepted technology for Internet of Things (IoT) networks worldwide.

The tracking device of the invention has a similar architecture as compared to prior RFID tags in that it includes a microcontroller, a radio transceiver, antenna, and a power source. One distinguishing feature however is time of flight measurements that are received by the radio transceiver and are communicated to the microcontroller for calculations that determine the position of the device. One method that can be used to determine location is triangulation wherein a tag is capable of being simultaneously interrogated by three RFID readers within the location where the tag is used.

A preferred spacial orientation of RFID readers is one in which all RFID tags can be continually monitored for changes in location wherein at least three RFID readers are capable of simultaneously interrogating any tag used within the location.

In accordance with another aspect of the invention, continual and uninterrupted tracking capabilities can be used to predict animal health. Categorizing potentially sick animals as opposed to healthy animals can be done by evaluation of animal movement data within the location. Healthy animals have a tendency to move around more than sick animals. Movement categories can be established to predict the likelihood that an animal may be sick. Recorded movements can then be compared to the movement categories as a predictive measure for analysis by a caregiver.

Another way to categorize potentially sick animals is to evaluate movement data within the location as to how often an animal remains at or approaches feed bins and water troughs. Sick animals under some circumstances do not drink or eat as much as normal. Feed and watering categories can also be established to predict the likelihood that an animal may be sick. Recorded movements of animals near feed bins and water troughs can be compared to the feed and watering categories.

Yet another way to categorize potentially sick animals is to evaluate movement data within the location as to how soon an animal approaches feed bins after a feed truck dispenses feed. It is also known that sick animals may wait until others are done feeding. Feed yards are competitive environments and healthy animals have a tendency to be more aggressive during feeding times. Recorded movements of an animal during feeding times can be used to indicate a behavior change and an early indication of sickness. Accordingly, animal movement categories during feeding can also be used to protect the likelihood that an animal may be sick.

There are other animal behaviors that may be detected based upon tracking movements of an animal. For example, an animal that remains alone and does not remain close to other animals may indicate sickness; the presence of a pen rider may stimulate sick animals to move and appear healthy to avoid being singled out as easy prey, it being understood that livestock maintain the instinct to herd together to avoid capture. Sick animals in a pen may fool a pen rider by looking healthy for the short period of time in which the pen rider is observing the animals, so therefore monitoring the animal during times in which there is no pen rider activity can also indicate whether an animal is sick.

The goal of the recorded observations regarding movement of each individual animal is to enable early detection of disease and therefore more timely treatment. Data can be generated resulting in graphical comparisons or numerical comparisons as to whether an animal has exhibited normal or predicted movement activity, or whether an animal shows observable changes in movement. The animals which exhibit abnormal movement can be sorted and evaluated by a caregiver.

Another advantage associated with use of longer range radio transceivers is that a fewer number of RFID readers are required. Installation and maintenance costs are therefore reduced in connection with setting up the location tracking system.

According to another aspect of the invention, it includes a capability to directly measure the temperature of an animal. The RFID device is used in combination with an implanted temperature sensor that communicates with the RFID device. There are existing RFID temperature sensors in use however significant drawbacks associated with such existing sensors because these sensors must also be positioned close to a RFID reader in 2.4 GHz radio transceivers. Further, it is been determined that the temperature of a cow varies during the day and can vary between about 3° F. Studies show that cows often go through a four to six hour cycle when temperature may rise and fall. It is therefore important that numerous temperature measurements be taken over the period of a day to account for the cyclical temperature changes.

In order to provide a temperature sensing capability without complete duplication of an RFID device, the present invention incorporates a temperature reader circuit that interrogates an implantable RFID temperature sensor located in close proximity to the location of the tag on the animal. For example, the implantable sensor can be located behind the ear of the animal approximately 1 to 2 inches from the location where the tag hangs from the ear of the animal. In order to overcome significant power requirements associated with successfully interrogating the RFID temperature sensor, the invention incorporates a low power solution to interrogate the RFID temperature sensor, as well as to produce power requirements for processing signals from the RFID temperature sensor. In one preferred embodiment, the RFID temperature sensor can be an inductive-capacitor (LC) sensor designed to vary slightly with temperature. The RFID device includes a temperature reader circuit with a driving coil for powering the LC sensor (and also functioning as the RFID antenna of the temperature reader circuit). The coil is driven using a driving circuit of the temperature reader circuit with signals conditioned by the microcontroller of the RFID device at a selected frequency. The coil generates a relatively weak magnitude electromagnetic field that is effective to power the LC sensor. Once the LC sensor is energized, the driving circuit in the RFID device is shut off. The LC sensor then begins to lose energy and will quickly return to its own resonant frequency. The LC sensor will generate signals corresponding to its resonance frequency as it decays from lack of power. Since the inductance of the LC sensor is fixed, the changing capacitance reflected in changes of the resonant frequency during decay can be directly correlated to temperature, since capacitance varies directly with temperature. The microcontroller of the RFID device is programmed to interrogate the LC sensor at repeated intervals in order to obtain a desired number of temperature readings of an animal over a designated period of time. By selectively cycling the driving circuit on and off, significant power is saved and therefore power can be preserved.

Calibration of the LC sensor is not critical since a cow's temperature can be monitored to obtain a baseline reading. Once a baseline reading is established, further monitoring can be conducted to determine if the temperature readings begin to deviate from an established normal. If elevated temperature patterns are observed, the animal can be pulled and treated. The capability to provide temperature monitoring with a very low power temperature sensor that is powered directly by the RFID location device prevents having to duplicate a dedicated RFID device that normally has much higher power requirements. Further, the microcontroller within the RFID location device can be programmed to handle not only location function logic, but also temperature function logic thereby eliminating a dedicated microcontroller associated with existing RFID temperature sensors.

In accordance with another aspect of the invention, a photovoltaic (PV) circuit may be integrated within the RFID location device to provide power to the device. One particular type of PV material that can be used within the invention includes flexible solar film that is very light and pliable. The body of the tag is made of a clear plastic in which the flexible solar film is encapsulated therein. Electrical energy created by the PV material is coupled with a capacitor to store electrical energy. The capacitor therefore replaces a battery that would normally power an RFID device. The microprocessor monitors power consumption and stored power to determine whether the PV circuit can generate enough power to be effectively interrogated. In the event the RFID location device has insufficient power, the microcontroller can be further programmed to shut off the device until the PV circuit can generate enough electrical power. For example, during the night or during low sunlight days, the device may not be sufficiently charged and during these times the device may automatically shut off. It is contemplated however that the selected flexible solar film is capable of generating enough power to prevent long shutdown periods yet the size of the animal tag that incorporates the RFID location device can still remain a manageable size.

Considering the above described features of the invention in various embodiments, in one aspect, the invention is an integrated RFID location device comprising an RFID microcontroller and data storage corresponding to at least one unique identifier for uniquely identifying the device, a low power, long range radio transceiver that communicates with a remote RFID reader, said transceiver when energized generating a signal to said RFID reader including a signal corresponding to said at least one unique identifier and a time of flight measurement, a photovoltaic (PV) circuit, a capacitor communicating with said PV circuit for storage of electrical energy generated by said PV circuit and for powering said microcontroller and said low power, long range transceiver, and a temperature reader circuit communicating with said microcontroller to transfer data to said microcontroller including temperature measurements received by said temperature reader circuit from a remote temperature sensor communicating with said temperature reader circuit.

According to another aspect of the invention, it may be considered an RFID location system comprising the above described RFID location device in combination with said RFID reader and said temperature sensor.

According to another aspect of the invention, it may be considered an RFID location and animal health monitoring system comprising the above described RFID location device in combination with said RFID reader, said temperature sensor, and the remote computing device communicating with said RFID reader wherein said remote computing device includes a data processing element, a data storage element, computer coded instructions that instruct triangulation processing by said data processing element to determine periodic locations of said RFID location device based on time of flight measurements received by said RFID reader and at least two other RFID readers communicating with said remote computing device, and a user output including at least one of information concerning measured temperature readings of a selected animal, an indication of health of the animal and location data indicating where the animal is located at various times over a selected period of time.

According to one preferred embodiment of the invention, it includes an RFID location tracking and health monitoring device for an animal comprising: a microcontroller with preprogrammed instructions for control of the device; a low power, long range transceiver electrically coupled to said microcontroller for communicating with a remote RFID reader to provide location data of said device; an antenna electrically coupled to said transceiver for receiving and transmitting radio signals of said low power, long range transceiver; a temperature reader circuit electrically coupled to said microcontroller, said temperature reader circuit producing an electromagnetic field at a desired frequency; a temperature sensor secured to the animal and inductively coupled to said temperature reader circuit, said temperature sensor including an inductor and a capacitor thereby forming an LC circuit; and wherein said temperature reader circuit includes a coil that is periodically energized to induce a voltage in said LC circuit, and said temperature reader circuit subsequently receives and records changes in capacitance of said LC circuit corresponding to a temperature of the animal.

According to another preferred embodiment of the invention, it includes a system providing RFID location tracking and health monitoring for animals comprising: (1) an RFID device having: (a) a microcontroller with preprogrammed instructions for control of the device; (b) a low power, long range transceiver electrically coupled to said microcontroller for communicating with a remote RFID reader to provide location data of said device; (c) an antenna electrically coupled to said transceiver for receiving and transmitting radio signals of said low power, long range transceiver; (d) a temperature reader circuit electrically coupled to said microcontroller, said temperature reader circuit producing an electromagnetic field at a desired frequency; (e) a temperature sensor secured to the animal and inductively coupled to said temperature reader circuit, said temperature sensor including an inductor and a capacitor thereby forming an LC circuit; wherein said temperature reader circuit includes a coil that is periodically energized to induce a voltage in said LC circuit, and said temperature reader circuit subsequently receives and records changes in capacitance of said LC circuit corresponding to a temperature of the animal; (2) an RFID reader communicating with said transceiver for receiving radio signals including identification data that uniquely identifies the animal and temperature data corresponding to temperature readings of the animal taken over a period of time; (3) a remote computing device communicating with said RFID reader that receives the identification data from said RFID reader and said temperature data, said remote computer device automatically generating at least one user output that provides a user with at least one of (a) information regarding the location and movement of the animal (b) temperature readings of the animal (c) indications of the health of the animal based on the temperature data and (d) further indications of the health of the animal based on typical or atypical movements of the animal.

According to another preferred embodiment of the invention, it includes a method for location tracking and health monitoring of an animal tagged with an RFD device, said method comprising: (1) providing an RFID device comprising: (a) a microcontroller with preprogrammed instructions for control of the device; (b) a low power, long range transceiver electrically coupled to said microcontroller for communicating with a remote RFID reader to provide location data of said device; (c) an antenna electrically coupled to said transceiver for receiving and transmitting radio signals of said low power, long range transceiver; (d) a temperature reader circuit electrically coupled to said microcontroller, said temperature reader circuit producing an electromagnetic field at a desired frequency; (2) securing the RFID device to the animal to be tracked and monitored; (3) interrogating the RFID device with an RFID reader and transmitting location data by said transceiver to said RFID reader; (4) communicating location data to a remote computing device that receives and records the location data to determine the location of the animal; (5) securing a temperature sensor to the animal; (6) inductively coupling said temperature reader circuit to said temperature sensor, said sensor including an inductor and a capacitor thereby forming an LC circuit; (7) selectively energizing a coil of said temperature reader circuit to produce the electromagnetic field and to induce a voltage in said LC circuit; and (8) said temperature reader circuit subsequently receiving and recording changes in capacitance of said LC circuit corresponding to a temperature of the animal.

According to yet another embodiment of the invention, it includes a method for health monitoring of an animal tagged with an RFD device and located within a known location, said method comprising: (1) providing an RFID device comprising: (a) a microcontroller with preprogrammed instructions for control of the device; (b) a low power, long range transceiver electrically coupled to said microcontroller for communicating with a remote RFID reader to provide location data of said device; (c) an antenna electrically coupled to said transceiver for receiving and transmitting radio signals of said low power, long range transceiver; securing the RFID device to the animal to be tracked and monitored; (2) interrogating the RFID device with an RFID reader and transmitting location data by said transceiver to said RFID reader; (3) communicating location data to a remote computing device that receives and records the location data to determine location changes of the animal; (4) establishing predicted movements of the animal while in the known location, said predicted movements including frequency of movement occurrences and distances travelled during said occurrences; (5) determining threshold values for movement occurrences and distances travelled over designated periods of time wherein sufficient values of movement occurrences or distances travelled indicate a healthy animal and insufficient values of movement occurrences or distances travelled indicate a potentially sick animal; (6) recording actual movement occurrences and distances travelled by the animal in said remote computer device by comparing said location changes over time; (7) comparing said actual movement occurrences and distances travelled by the animal against said threshold values; (8) automatically determining whether said actual movement occurrences and distances travelled by the animal have a value that is sufficient or insufficient; and (9) automatically generating a message to other communication devices by said remote computer device that indicates whether the animal is healthy or potentially sick.

According to yet another preferred embodiment of the invention relating to the method for health monitoring of an animal tagged with an RFD device and located within a known location, the method may further comprise the steps of: (1) providing a temperature reader circuit electrically coupled to said microcontroller, said temperature reader circuit producing an electromagnetic field at a desired frequency; (2) securing a temperature sensor to the animal, said sensor including an inductor and a capacitor thereby forming an LC circuit; (3) inductively coupling said temperature reader circuit to said temperature sensor; (4) selectively energizing a coil of said temperature reader circuit to produce the electromagnetic field and to induce a voltage in said LC circuit, wherein said temperature reader circuit subsequently receives and records changes in capacitance of said LC circuit corresponding to a temperature of the animal; (5) comparing the temperature of the animal to said sufficient or insufficient value; and (6) automatically generating another message to said other communication devices by said remote computer device that further indicates whether the animal is healthy or potentially sick also considering whether the temperature of the animal is normal or abnormal.

Other features and advantages of the invention will become apparent from a review of the following detailed description taken in conjunction with the drawings.

DETAILED DESCRIPTION

Figure 1:
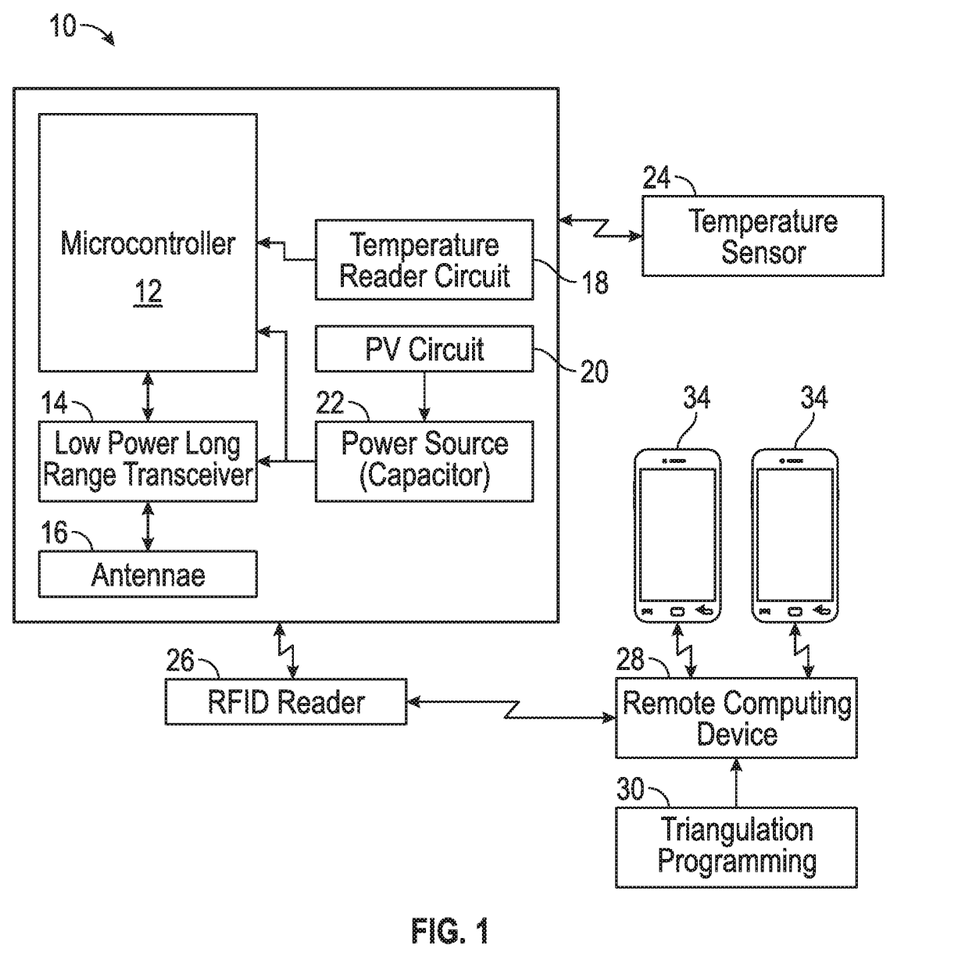
FIG. 1 is a schematic diagram of the RFID location device and system of the invention.

FIG. 1 is a schematic diagram of the RFID location device and system according to preferred embodiments of the invention. The location device 10 has functional components that enable the device to locate a tagged object and to record temperature measurements from a remote temperature sensor. The location and temperature data are communicated to a remote computing device for analysis and to conduct follow-up actions. For example, the location device 10 of the invention is especially adapted for use with tagging livestock such as cattle located in a feed yard wherein the remote computing device is a central feed yard computer that handles management of cattle within the feed yard and specifically manages cattle movement, feeding, and treatment.

The device 10 is shown as including a microcontroller 12 that is a programmable controller for handling all of the location tracking functions as well as temperature recording functions. A low power, long range radio transceiver 14 communicates with the microcontroller 12. In turn, transceiver 14 communicates with one or more remote RFID readers 26 via antenna 16. The RFID reader 26 incorporates a long range transceiver that is configured to receive RFID signals from a plurality of location devices that each incorporate their own transceivers. The RFID reader 26 communicates with one or more remote computing devices 28 that process data associated with what is communicated from the location devices 10 and temperature sensing devices 24. Thus, the remote computing device(s) may include data processors, data storage devices, user interfaces, and other known computing device elements associated with a central processing computer that controls a plurality of field devices. A number of mobile communication devices 34 may in turn communicate with the remote computing device 26 in order to receive messages or updates generated from the remote computing device(s) regarding the location and health status of animals being tracked. Special programming may be added to the remote computing devices in order to manage tracking functions, such as triangulation programming 30 and others.

The device 10 is further shown as having a temperature reader circuit 18 that communicates with the remote temperature sensor 24 to generate an electromagnetic field that activates the temperature sensor 24. The temperature reader circuit receives a return data signal from the temperature sensor 24 and conveys the data to the microcontroller 12. A photovoltaic circuit (PV) 20 is also shown as one method of powering the location device 10. The PV circuit includes an array of photovoltaic cells 21 (FIG. 2) that convert sunlight to electrical energy. The electrical energy may be stored in a capacitor 22.

The temperature sensor 24 is used to monitor temperature of the animal in which the sensor is installed. According to one preferred embodiment the sensor 24 is an inductive coupled sensor that incorporates an LC circuit. Accordingly, the sensor 24 includes an inductor and a capacitor. The temperature reader circuit 18 has a coil that produces an interrogation or driver signal at a preset frequency to energize the LC circuit. The coil when energized generates a small electromagnetic field that induces a voltage in the LC circuit. The driver signal is shut off and the LC circuit in the sensor begins to lose energy. The LC circuit quickly returns to its own resonant frequency as it decays. The transmitted resonant frequency of the LC circuit as is received and recorded by the temperature reader circuit. Since the inductance L is fixed in the LC circuit, the variable is the capacitance C. Capacitance varies with temperature so the temperature can be determined from the measured capacitance. The driving coil of the temperature reader circuit is periodically energized and de-energized in order to obtain the measured capacitance of the sensor over a period of time. The on-off cycling of the temperature reader circuit consumes very low power as compared to continually powering the temperature reader circuit. Nonetheless, the temperature reader circuit still generates an additional load on the identification device and therefore, the use of a photovoltaic circuit with use of flexible solar film is a cost-effective yet effective solution for producing adequate power. The power source 22 may be a "super capacitor" which is known in consumer electronics as a relatively lightweight and small capacitor that can be easily incorporated on the structure of the standard livestock tag.

Figure 2:
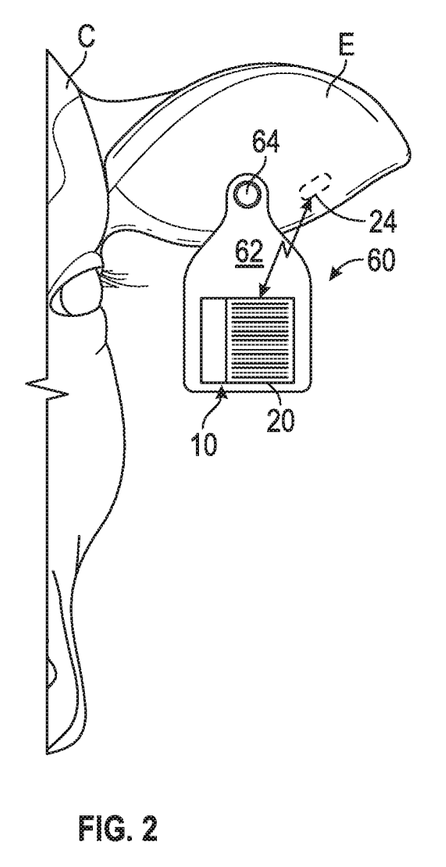
FIG. 2 is a schematic diagram of the RFID location device as incorporated within an example animal tag.

FIG. 2 is a schematic diagram of the RFID location device 10 as incorporated within an exemplary animal tag 60. More specifically, the tag 60 is an ear tag installed on the ear of livestock. The tag 60 as depicted in the figure is connected to the ear E of an animal such as a cow C. The tag 60 is typically attached to the front side of the ear E as shown in which a connector 64 secures the tag that hangs below the connector 64. The tag body 62 is typically made of a flexible plastic material. The identification device 10 may be encapsulated within the tag body. Preferably, the tag body 62 is made of a clear plastic that enables light to pass through it to the PV circuit 20. It should be understood that the particular size and shape of the identification device 10 is only exemplary, and both the size and orientation of the identification device 10 and tag body 62 can be modified to ensure that the PV circuit 20 is large enough that it may adequately power the device 10. Further, while the tag 60 is shown as a traditional hang tag, the invention is not strictly limited to hang tags and may be used with other type of identification tags. The temperature sensor 24 is also illustrated in which it is secured to the rear side of the animal's ear and in close proximity to the identification device 10. In order to maintain an adequate inductive coupling between the sensor 24 and the temperature reader circuit, the temperatures sensor should be located within a few inches of the temperature reader circuit. Locating the temperature sensor 24 on the rear side of the ear E is a convenient location where the sensor 24 may be best protected yet placed in close proximity to the device 10. Although the RFID location device 10 is shown as incorporated in an ear tag 60, it should be understood that the RFID location device 10 can be used with any type of identification device for livestock or other animals. For example, the RFID location device could be incorporated in a back tag that is secured to the animal's back and the temperature sensor 24 could be embedded in the tissue of the animal's back just below the location of the RFID location device.

Figure 3:
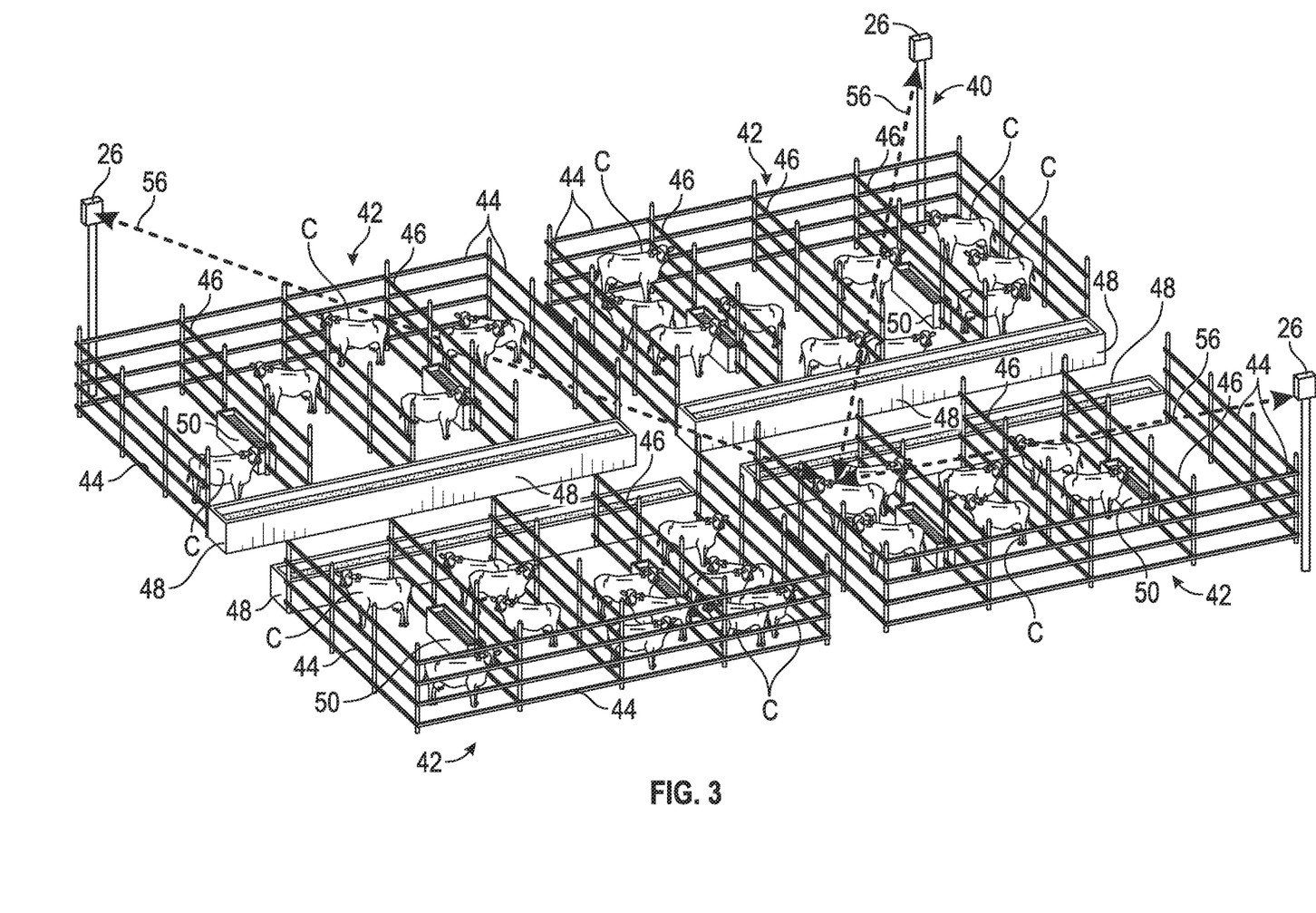
FIG. 3 is another schematic diagram of a location such as a feed yard where the RFID location device and system may be used, and more specifically showing a simplified illustration of triangulation wherein multiple RFID readers are capable of interrogating an RFID location device for precise location identification and monitoring.

FIG. 3 is a schematic diagram of a location such as a feed yard 40 where an RFID location device and system may be used, and more specifically showing a simplified illustration of triangulation wherein multiple RFID readers 26 are capable of interrogating an RFID location device 10 for precise location identification and monitoring of an animal. For illustration purposes, the feed yard 40 is not to scale, and is intended to illustrate however a basic layout of a feed yard in which multiple animals such as cattle C are co-located. A feed yard can be quite large, extending over multiple kilometer distances. The feed yard 20 may contain a plurality of separate pens 42 each containing sorted cattle C each in various stages of production. Each pen 42 is separated from other pens by perimeter fencing 44 and each pen may have one or more separate dividers 46 further segregating cattle C within a particular pen 42. Feed pens 48 are typically located along one common side of adjacent pens which allows feed trucks to more easily service each of the pens with daily feed. Each of the pens further includes various watering points 50 which can be placed directly adjacent the feed pens 48 or at other locations within the pens. Throughout the feed yard there may be a number of RFID readers located to interrogate the identification devices 10 of each of the tag animals. The RFID readers 26 are deliberately spaced in a pattern such that each of the readers 26 may effectively interrogate an identification device 10 located at any point location within the feed yard. FIG. 3 further shows example interrogation signals 56 that allow three illustrated readers 26 to simultaneously interrogate the identification device on a tag of one of the animals as shown. By use of long range transceivers in each of the devices 10, each of the animals within the feedlot can be tracked as to their specific location at any time.

According to preferred embodiments of the invention with respect to the system and method, the continual and uninterrupted tracking capabilities can be used to predict animal health. Animal movement data can be recorded in the remote computing device 28 based on data from each of the identification devices 10 as conveyed by the RFID readers 26. The recorded movements can be sorted for each identification device which provides a record of moment for each individual animal. It is known that healthy animals have a tendency to move around more than sick animals. Considering this tendency, potentially sick animals can be identified based upon predetermined categories as to the frequency of animal movement as well as distance traveled for each of the movements. For example, the predetermined categories can set numerical values as to frequency and distance for a specified period of time. Automatic calculations can be conducted for distance and frequency movements for each animal such that an animal can be categorized as being potentially sick or healthy. Reporting can be automatically provided in the event any animal is categorized as being potentially sick. Reporting can be achieved in the form of electronic reporting by user interfaces associated with the system, such as user portals, smart phones, and other electronic devices. For example, if a particular animal is identified as potentially sick, the remote computing device can automatically generate an alert identifying the animal wherein the alert is distributed to electronic communication devices that are incorporated within the system, shown as the mobile communication devices 34 of FIG. 1.

Another way to categorize potentially sick animals is to evaluate movement data within the location as to how often an animal remains at or approaches feed bins 48 and water troughs 50. Sick animals under some circumstances do not drink or eat as much as normal. Feed and watering categories can also be established to predict the likelihood that an animal may be sick. Recorded movements of animals near feed bins and water troughs can be compared to the feed and watering categories.

Yet another way to categorize potentially sick animals is to evaluate movement data within the location as to how quickly or slowly an animal approaches feed bins after feed has been dispensed. Sick animals are known to hesitate to feed until others are done feeding since the feed yards are competitive environments and healthy animals have a tendency to be more aggressive during feeding times. The recorded movements of animals can therefore be further analyzed as to the frequency and distance an animal may travel during feeding times. Animal movement categories during feeding can also be used to predict the likelihood that an animal may be sick.

Other animal behaviors that may be tracked and recorded based upon detected movements of an animal. For example, an animal that remains alone and does not choose to herd with other animals may indicate sickness. A pen rider may stimulate sick animals to move and appear healthy to avoid being singled out as easy prey, since livestock maintain the instinct to herd together to avoid capture. Accordingly, a sick animal in a pen may fool a pen rider by looking healthy for the short period of time in which the pen rider is observing the animals, however once the pen rider was on, the animal may return to its generally lethargic movements. A spike or atypical group of movements associated with pen rider activity may therefore indicate the presence of a sick animal. Again, movement categories can be established with the addition of a pen rider variable wherein movements are evaluated in light of the pen rider variable and comparison of animal movements without the presence of a pen rider.

According to another aspect of the invention, an RFID reader used to triangulate the location of RFID location devices could include an RFID reader that is carried by pen riders who conduct daily inspections of animals at locations such as feed yards. Pen riders may carry mobile communication devices that are used to record and convey data and observations regarding the health of animal. The mobile communication devices may have the capability to automatically upload data and observations via a wireless network to a central computer of the feed yard that manages the feeding, sorting, and treatment of the animals. According to the invention, the mobile communication devices of the pen riders may be supplemented with an RFID reader capability or the pen riders could carry dedicated RFID reader devices. The use of mobile RFID readers could simplify the array of RFID readers used in a feed yard and thereby reduce the number of static RFID readers employed.

According to yet another aspect of the invention, pen riders could be equipped with active RFID tags or enhanced passive RFID tags that could be used as a beacon to help identify a particular animal that required identification for sorting or treatment. For example, if triangulation techniques were not able to consistently identify the location of one or more animals located at a remote location of a feed yard, the pen rider could travel to the remote location and position him/herself close to the animal requiring identification. Once co-located at the desired location, the system could identify the pen rider as the beacon and then triangulate the location to confirm the location of the tagged animal in question.

Considering the foregoing, there are many advantages of the invention over the prior art. The long range RFID capability enables traditional RFID tags to have functionality that goes beyond mere identification, but also adds a location tracking capability. Use of a photovoltaic element eliminates the need for a large battery. Additional functionality is achieved with the temperature reader circuit wherein the temperature of an animal may be selectively monitored without requiring the use of a separate RFID temperature sensor. Temperature monitoring combined with analyzing pre-categorized animal movements provide yet another measure of animal health for early detection of potentially diseased animals. Each of the foregoing are realized within an RFID system that does not require special equipment or excessive power requirements.

Although the invention has been described with respect to various embodiments, it should be understood that the invention is not strictly limited to these embodiments. Therefore, the invention can be broadened or modified commensurate with the scope of the claims appended hereto.

What is claimed is:

1. An RFID location tracking and health monitoring device for an animal comprising:
   a tag body;
   a microcontroller with preprogrammed instructions for control of the device mounted on said tag body;
   a transceiver electrically coupled to said microcontroller on said tag body for communicating with a remote RFID reader to provide location data of said device;
   an antenna electrically coupled to said transceiver for receiving and transmitting radio signals of said transceiver;
   a temperature reader circuit connected to and electrically coupled to said microcontroller on said tag body, said temperature reader circuit producing an electromagnetic field at a desired frequency;
   a temperature sensor secured to the animal and spaced from said tag body, and inductively coupled to said temperature reader circuit, said temperature sensor including an inductor and a capacitor thereby forming an LC circuit; and
   wherein said temperature reader circuit includes a coil that is periodically energized to induce a voltage in said LC circuit, and said temperature reader circuit subsequently receives and records changes in capacitance of said LC circuit corresponding to a temperature of the animal.

2. The device, as claimed in claim 1, further including:
   a photovoltaic (PV) circuit to provide power to said device, and a capacitor electrically coupled to said PV circuit to store electrical energy created by said PV circuit.

3. The device, as claimed in claim 2, wherein:
   said PV circuit includes a PV array comprising a flexible film material.

4. The device, as claimed in claim 2, wherein:
   said tag body includes an animal identification tag made of a flexible clear thermoplastic material wherein said device is encapsulated in said tag and said tag includes a PV array that is energized by sunlight striking said PV array through said flexible clear thermoplastic material.

5. A system providing RFID location tracking and health monitoring for animals:
   an RFID device mounted on a tag body, said RFID device comprising: (a) a microcontroller with preprogrammed instructions for control of the device; (b) a transceiver electrically coupled to said microcontroller for communicating with a remote RFID reader to provide location data of said device; (c) an antenna electrically coupled to said transceiver for receiving and transmitting radio signals of said transceiver; (d) a temperature reader circuit connected to and electrically coupled to said microcontroller, said temperature reader circuit producing an electromagnetic field at a desired frequency; (e) a temperature sensor secured to the animal and inductively coupled to said temperature reader circuit, said temperature sensor including an inductor and a capacitor thereby forming an LC circuit; wherein said temperature reader circuit includes a coil that is periodically energized to induce a voltage in said LC circuit, and said temperature reader circuit subsequently receives and records changes in capacitance of said LC circuit corresponding to a temperature of the animal;
   an RFID reader communicating with said transceiver for receiving radio signals including identification data that uniquely identifies the animal and temperature data corresponding to temperature readings of the animal taken over a period of time; and
   a remote computing device communicating with said RFID reader that receives the identification data from said RFID reader and said temperature data, said remote computer device automatically generating at least one user output that provides a user with at least one of (a) information regarding the location and movement of the animal (b) temperature readings of the animal (c) indications of the health of the animal based on the temperature data and (d) further indications of the health of the animal based on typical or atypical movements of the animal.

6. A method for location tracking and health monitoring of an animal tagged with an RFID device, said method comprising:
   providing an RFID device mounted on a tag body comprising: (a) a microcontroller with preprogrammed instructions for control of the device; (b) a transceiver electrically coupled to said microcontroller for communicating with a remote RFID reader to provide location data of said device; (c) an antenna electrically coupled to said transceiver for receiving and transmitting radio signals of said transceiver; (d) a temperature reader circuit connected to and electrically coupled to said microcontroller, said temperature reader circuit producing an electromagnetic field at a desired frequency;
   securing the RFID device to the animal to be tracked and monitored;

interrogating the RFID device with an RFID reader and transmitting location data by said transceiver to said RFID reader;
communicating location data to a remote computing device that receives and records the location data to determine the location of the animal;
securing a temperature sensor to the animal;
inductively coupling said temperature reader circuit to said temperature sensor, said sensor including an inductor and a capacitor thereby forming an LC circuit;
selectively energizing a coil of said temperature reader circuit to produce the electromagnetic field and to induce a voltage in said LC circuit; and
said temperature reader circuit subsequently receiving and recording changes in capacitance of said LC circuit corresponding to a temperature of the animal.

7. A method for health monitoring of an animal tagged with an RFD device and located within a known location, said method comprising:
providing an RFID device mounted on a tag body comprising: (a) a microcontroller with preprogrammed instructions for control of the device; (b) a transceiver electrically coupled to said microcontroller for communicating with a remote RFID reader to provide location data of said device; (c) an antenna electrically coupled to said transceiver for receiving and transmitting radio signals of said transceiver; securing the RFID device to the animal to be tracked and monitored; (d) a temperature reader circuit connected to and electrically coupled to said microcontroller, said temperature reader circuit producing an electromagnetic field at a desired frequency;
interrogating the RFID device with an RFID reader and transmitting location data by said transceiver to said RFID reader;
communicating location data to a remote computing device that receives and records the location data to determine location changes of the animal;
establishing predicted movements of the animal while in the known location, said predicted movements including frequency of movement occurrences and distances travelled during said occurrences;
determining threshold numerical values for movement occurrences and numerical values for distances travelled over designated periods of time wherein sufficient numerical values of movement occurrences or distances travelled indicate a healthy animal and insufficient numerical values of movement occurrences or distances travelled indicate a potentially sick animal;
recording actual movement occurrences and distances travelled by the animal in said remote computer device by comparing said location changes over time;
comparing said actual movement occurrences and distances travelled by the animal against said threshold numerical values;
automatically calculating whether said numerical values for actual movement occurrences and distances travelled by the animal have numerical values that are sufficient or insufficient; and
automatically generating a message to other communication devices by said remote computer device that indicates whether the animal is healthy or potentially sick.

8. The method, as claimed in claim 7, further including the steps of:
securing a temperature sensor to the animal, said sensor including an inductor and a capacitor thereby forming an LC circuit;
inductively coupling said temperature reader circuit to said temperature sensor;
selectively energizing a coil of said temperature reader circuit to produce the electromagnetic field and to induce a voltage in said LC circuit, wherein said temperature reader circuit subsequently receives and records changes in capacitance of said LC circuit corresponding to a temperature of the animal;
comparing the temperature of the animal to said sufficient or insufficient value; and
automatically generating another message to said other communication devices by said remote computer device that further indicates whether the animal is healthy or potentially sick also considering whether the temperature of the animal is normal or abnormal.

9. An RFID location tracking and health monitoring device for an animal comprising:
a tag body;
a microcontroller with preprogrammed instructions for control of the device mounted on said tag body, said control including location tracking functions and temperature recording functions;
a transceiver electrically coupled to said microcontroller on said tag body for communicating with a remote RFID reader to provide location data of said device;
an antenna electrically coupled to said transceiver for receiving and transmitting radio signals of said transceiver;
a temperature reader circuit connected to and electrically coupled to said microcontroller on said tag body, said temperature reader circuit producing an electromagnetic field at a desired frequency;
a temperature sensor secured to the animal and spaced from said tag body, and inductively coupled to said temperature reader circuit, said temperature sensor including an inductor and a capacitor thereby forming an LC circuit;
said electromagnetic field being a driver signal to energize said LC circuit; and
wherein said temperature reader circuit includes a coil that is periodically energized to produce said electromagnetic field and to thereby induce a voltage in said LC circuit to energize said LC circuit, and said temperature reader circuit subsequently receives and records changes in capacitance of said LC circuit corresponding to a temperature of the animal, said changes being conveyed as data to said microcontroller.

* * * * *